United States Patent [19]

Sandow et al.

[11] Patent Number: 5,091,365
[45] Date of Patent: Feb. 25, 1992

[54] CYCLIC PEPTIDES AS PROMOTERS OF ABSORPTION ON ADMINISTRATION ONTO THE MUCOSA

[75] Inventors: Jürgen K. Sandow, Königstein/Taunus; Rainer Schmiedel, Kelkheim; Klaus Wirth, Frankfurt am Main; Hans P. Merkle, Frankfurt am Main; Suzanne Raehs, Bonn, all of Fed. Rep. of Germany

[73] Assignee: Hoechst Aktiengesellschaft, Frankfurt, Fed. Rep. of Germany

[21] Appl. No.: 228,651

[22] Filed: Aug. 5, 1988

[30] Foreign Application Priority Data

Aug. 7, 1987 [DE] Fed. Rep. of Germany ....... 3726324

[51] Int. Cl.$^5$ .......................... C07K 5/12; A61K 37/02
[52] U.S. Cl. ........................................ 514/9; 514/12; 514/13
[58] Field of Search ................. 514/9, 12, 13

[56] References Cited

U.S. PATENT DOCUMENTS

| | | | |
|---|---|---|---|
| 4,434,159 | 2/1984 | Sekine et al. | 424/178 |
| 4,537,772 | 8/1985 | Alexander et al. | 514/9 |
| 4,613,500 | 9/1986 | Suzuki et al. | 429/85 |
| 4,789,667 | 12/1988 | Makino et al. | 514/161 |
| 4,900,730 | 2/1990 | Miyauchi | 514/12 |

FOREIGN PATENT DOCUMENTS

| | | |
|---|---|---|
| 0159167 | 10/1985 | European Pat. Off. |
| 3532074A1 | 3/1987 | Fed. Rep. of Germany |
| 2095994 | 10/1982 | United Kingdom |
| 2180746A | 4/1987 | United Kingdom |

OTHER PUBLICATIONS

J. Sandow, W. Petri, "Intranasal Administration of Peptides Biological Activity and Therapeutic Efficacy", Transnasal Systemic Medications, pp. 183-199 (1985).
Chemical Abstracts, Pharmaceuticals for Rectal Application, vol. 97, p. 400, 97:98358y.

*Primary Examiner*—Lester L. Lee
*Assistant Examiner*—A. Davenport
*Attorney, Agent, or Firm*—Finnegan, Henderson, Farabow, Garrett and Dunner

[57] ABSTRACT

The invention relates to the use of aids of the general formula $$\text{cyclo-(B—A/B—X—NH(CH}_2)_{2-4}\text{—CH—CO—B—L—L)} \atop {\underset{R}{\underset{|}{\text{NH}}}}$$

in which B denotes a basic amino acid, A/B denotes an acidic or basic amino acid, X denotes a neutral and hydrophilic amino acid, L denotes a lipophilic neutral amino acid, and R denotes hydrogen or an acyl radical, or the physiologically tolerated salts thereof, for promoting the absorption of peptides and proteins on administration onto the mocosa, as well as to pharmaceutical compositions which contain a pharmacologically effective amount of one or more peptides or proteins as well as an aid of the abovementioned formula.

9 Claims, No Drawings

CYCLIC PEPTIDES AS PROMOTERS OF ABSORPTION ON ADMINISTRATION ONTO THE MUCOSA

The invention relates to aids, especially cyclic peptides, for promoting absorption of peptides and proteins on administration onto the mucosa.

The use of peptides and proteins as medicaments is considerably impeded by the problems of a suitable pharmaceutical formulation from which the peptide or protein which is to be used for therapy or diagnosis is absorbed reliably and in sufficient amount.

A solution corresponding to the state of the art is the administration of one or more single doses each day by nasal administration, whether in the form of nose drops or by spraying a suitable solution into the nose (J. Sandow, W. Petri in Transnasal Systemic Medications, published by Elsevier, (1985) 183-199). It is known to use for this purpose well-tolerated aqueous solutions with the addition of preservatives. The known aids for increasing absorption (absorption enhancers) are all irritant to the mucosa or unsuitable due to an unpleasant odor or taste, and they often give rise, even on a single administration, to considerable pain and lacrimation or, on multiple administration, bring about progressive irritation and inflammation of the nasal mucosa. This applies, for example, to derivatives of fusidic acid and to gallic acids and various glycols (polyethylene glycol and propylene glycol).

The invention has the object of finding aids which promote absorption on administration onto the mucosa and are well tolerated, i.e. are not irritant to the mucosa.

This object is achieved according to the invention by using aids of the general formula I

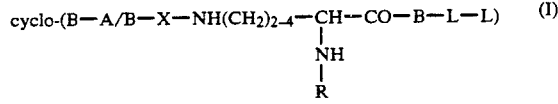

in which
B denotes a basic amino acid,
A/B denotes an acidic or basic amino acid,
X denotes a neutral and hydrophilic amino acid,
L denotes a lipophilic neutral amino acid, and
R denotes hydrogen or an acyl radical,
as well as the physiologically tolerated salts thereof.

Preferred radicals B, A/B, X and L are those which are derived from naturally occurring amino acids (see, for example, Schröder, Lübke, The Peptides, Volume I, New York 1965) and 2,4-diaminobutyric acid, and the antipodes and simple metabolites thereof, which can, if chiral, be in the D or L form.

Unless otherwise indicated, the three-letter symbols (cf. for example, Pure & Appl. Chem. 56 (1984) 595-624 and Eur. J. Biochem. 138 (1984) 9-37) are used hereinafter for the residues of the amino acids. The symbol "D" prefixes these symbols when the residue is that of a D-amino acid; residues without a configuration symbol have the L configuration.

Preferred compounds of the formula I are those in which
B denotes lysine, ornithine, histidine, 2,4-diaminobutyric acid or arginine,
A/B denotes lysine, ornithine, histidine, 2,4-diaminobutyric acid, arginine, aspartic acid or glutamic acid,
X denotes asparagine, glutamine, serine or threonine,
L denotes leucine, isoleucine, valine, threonine, phenylalanine or tryptophan, and
R denotes hydrogen or an acyl radical having the following structures

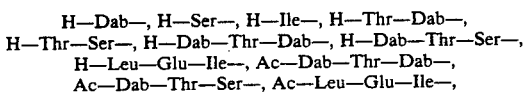

it being possible for each of the amino acids to be in the D or L form.
In this context, Ac represents

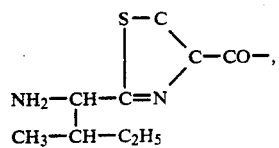

it being possible for S also to be in the form of the sulfoxide or sulfone, and for the double bond to be hydrogenated,

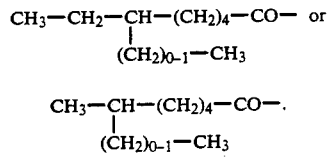

Particularly suitable have proved to be the bacitracins, colistins, circulins and polymyxins known as peptide antibiotics [R. Reiner, Antibiotica and ausgewählte Chemotherapeutica (Antibiotics and Selected Chemotherapeutics), published by Georg Thieme Stuttgart] such as, for example, bacitracin A:

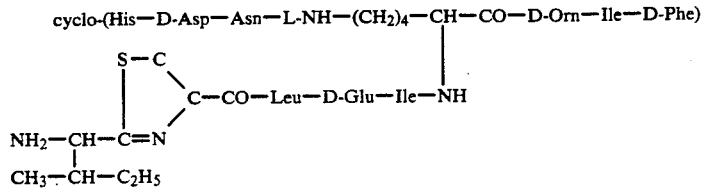

colistin A or B:

-continued

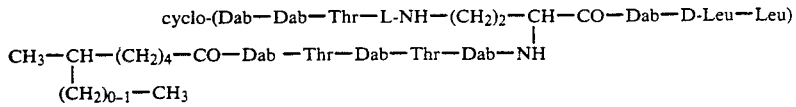

circulin A or B:

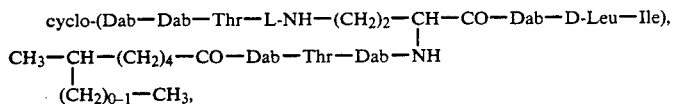

polymyxin B₁ or B₂:

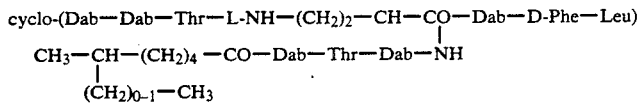

polymyxin D₁ or D₂:

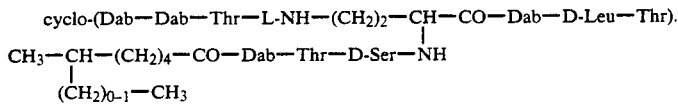

Because of the diminished antibiotic action and toxicity, also of interest are the cyclic peptides of the general formula I with the side chain partially or completely degraded [T. Suzuki et al., J. Biochem. Tokyo 54 (1963) 555; 56 (1964) 335; S. T. Chihara et al., Agr. Biol. Chem. 37 (1973) 2455-2463; M. Vaara and T. Vaara, Antimicrobial Agents and Chemotherapy 24 (1983) 107-113], such as, for example, polymyxin B nonapeptide (PMBN) or polymyxin B heptapeptide (PMBH).

Polymyxin B nonapeptide (PMBN):

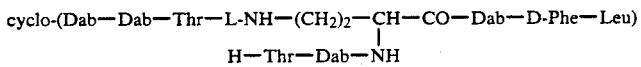

polymyxin B heptapeptide (PMBH):

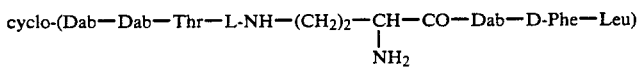

The compounds according to the invention can be prepared using the general methods of peptide chemistry (Houben-Weyl, Methoden der organischen Chemie (Methods of Organic Chemistry), 15/1 and 2), for example stepwise from the C-terminal end or by segment condensation followed by cyclization as described, for example, in EP-A 87 106 224.6, or by isolation followed by degradation—where appropriate by enzymatic cleavage—of the corresponding naturally occurring peptides [T. Suzuki et al., J. Biochem. Tokyo 54 (1963) 555; 56 (1964) 335; S. T. Chihara et al., Agr. Biol. Chem. 37 (1973) 2455-2463; M. Vaara and T. Vaara Antimicrobial Agents and Chemotherapy 24 (1983) 107-113].

The compounds according to the invention make a quite considerable contribution to improving the absorption of peptides and proteins on administration onto the mucosa. Thus, the increase in the activity of the peptides or proteins after addition of the compounds according to the invention is 300 to 400% and may in individual cases be more than 1000%. An increase in activity has been demonstrated, for example, for LHRH (gonadoliberin), LHRH agonists (buserelin and similar nona- and decapeptides), growth hormone releasing hormone and agonists, ACTH (corticotropin) and agonists, and calcitonin and agonists.

EXAMPLES

1. The effect of cyclic peptides on the nasal and rectal absorption of LHRH (gonadorelin) and LHRH agonists (for example buserelin) was investigated in the following way: female rats weighing 60 g are pretreated with horse serum gonadotropin (PMSG) 10 I.U. (day 1, 09:00) for follicle stimulation. On the third day after the pretreatment, the ovulation which spontaneously occurs at about 14:00 is suppressed by injection of phenobarbital (4 mg/animal i.p. around 13:00). The treatment with the test substance (for example LHRH or buserelin intranasally in a physiologically tolerated buffer solution of pH 3.0-7.5 in a volume of 2-20 µl, rectal administration of suppositories etc.) is carried out at about 13:30. This treatment induces ovulation dose-dependently. On the next day of the experiment (day 4) the animals are sacrificed at about 09:00, both uterine tubes are dissected out and, after staining with patent blue, the number of ova is counted under a stereomicroscope (ovulatory effect of the test substances). The increase in the absorption of the test substances from mucosal surfaces is assessed by comparison of the effect on ovulation in the absence or after addition of, for example, bacitracin 0.001-0.05M. It is also possible to use as parameter of the effect in the same design of experiment the dose-dependent increase in luteinizing hormone (LH) in the serum one hour after treatment. [Sandow J, von Rechenberg W & Jerzabek G (1976): The effect of LHRH, prostaglandins and synthetic analogues of LHRH on ovarian metabolism. Europ. J. Obstetr. Gynaec. Reprod. Biol. 6, 185-190.]

It emerged that, in this design of experiment, the ovulatory effect of 8 μg of LHRH in physiological saline containing 0.1% gelatin is the same as the effect of 2 μg of LHRH in a solution of 0.001M bacitracin. Furthermore, this effect also emerged in the presence of 0.001M colistin on investigation of the LH release. Likewise, in this design of experiment, the ovulatory effect of 80 ng of buserelin in physiological saline containing 0.1% gelatin corresponded to the effect of 20 ng of buserelin in a solution of 0.001M bacitracin. The enhancement of absorption also emerged from the determination of LH release by buserelin in the presence of 0.001M bacitracin. In this case the enhancement was by a factor of more than 3.

2. An example of another method suitable for detecting the enhancement of the effect due to increased absorption is determination of the LH release in male rats (weighing 100 g, under urethane anesthesia). This entails comparison of the hormone release over a period of 6-7 hours after treatment (for example by nasal or rectal administration of the test substances in physiological saline with or without addition of bacitracin, polymyxin B or similar cyclic peptides). It emerged that both bacitracin and colistin and polymyxin B (0.01M) increased the effect of a dose of 10 ng of buserelin, measured by the areas under the curve, by a factor of 3.3-14.

On rectal treatment of rats with buserelin suppositories in the same model, ovulation occurred at a dose of 400 ng without addition of bacitracin, whereas ovulation was induced at a dose of only 50 ng of buserelin after addition of bacitracin.

3. The effect of cyclic peptides of the nasal absorption of GHRH analogs was investigated in the following way: In the same model as described for the ovulatory effect of LHRH, it is possible on the third day after the pretreatment with PMSG to test the release of growth hormone (GH). GH in serum is determined 15-120 minutes after the treatment (for example nasally or rectally) by a specific radioimmunoassay.

It emerged that the effect of (DAla2) GRF-29 amide at a dose of 40 μg i.n. without bacitracin corresponded to the effect of a dose of 20 μg with the addition of 0.001M bacitracin. The finding was similar with other GHRH agonists, for example with (DAla2, NLeu27) GRF-29 amide and the GHRH derivative (Leu27, Gly45) GHRH (1-44) prepared by genetic manipulation.

4. The effect of cyclic peptides on the absorption of ACTH (corticotropin) and ACTH analogs was investigated in male rats (weighing 100 g) after treatment under anesthesia with pentobarbital or ether. The corticosterone release in the serum was determined by a specific radioimmunoassay as a parameter of the effect. It emerged that the corticosterone release over 3 h after nasal treatment, for example, with the ACTH analog alsactide (ACTH-17) in a dose of 5 μg was increased by a factor of 5 in the presence of 0.01M bacitracin.

5. The effect of cyclic peptides on the absorption of calcitonin and calcitonin analogs (for example salmon calcitonin) can be investigated on male rats weighing 100 or 200 g, for example after intranasal treatment with salmon calcitonin, by determination of the serum calcium concentration over a period of 1-6 h after the treatment. It was found in this that the effect of 0.6-1.2 μg of salmon calcitonin was increased by a factor of 4-6 by addition of, for example, 0.01M bacitracin.

6. The tolerability of various cyclic peptides as are used as aids to increase absorption can be tested on the isolated gastric mucosa of the guinea pig. [Wirth K, Bickel M & Deutschländer N (1987): Patent blue permeation through the isolated guinea pig gastric mucosa: a quantitative method for the assessment of gastric irritants. Med. Sci. Res. 15, 881.]

It emerged from this that gallic acids, for example deoxycholic acid which greatly increases absorption, cause, at a concentration as low as 0.002M, mucosal damage which results in increased permeation of patent blue, whereas a 10-fold higher concentration of 0.02M is required to increase absorption in the rat, for example tested with the LHRH analog buserelin. In contrast, a concentration of more than 0.006M bacitracin can be placed on the mucosa without damage, whereas addition of as little as 0.001M bacitracin increases the absorption, for example of LHRH agonists, GHRH agonists and similar active substances, by a factor of 3-4.

Furthermore, the compounds according to the invention cause no sensation of pain in humans on nasal administration of 1 to 200 μl of a concentration of $10^{-5}$ to $10^{-1}$ mol/l. As shown in Example 6, they do not cause any damage in the model of the isolated gastric mucosa. Local administration of the same concentration by vaginal, rectal or buccal drug forms (i.e., for example, films, tablets, suppositories) likewise causes no irritation to the mucosa. On rectal administration of hard fat suppositories with an active substance content of 1 mg of bacitracin in rats weighing 100 g, no inflammatory change of the rectal mucosa was found 3 hours after the treatment. The absorption-promoting effect of the compounds according to the invention was also demonstrated in a test model as described, for example, in "Transnasal Systemic Medications" (edited by Y. W. Chien, published by Elsevier, 1985), in rats and in humans too.

It is possible and appropriate for most of the currently known peptides and proteins which are used, or will be used in the near future, as therapeutic or diagnostic agents to be administered onto the mucosa, such as, for example, nasal, buccal, rectal or vaginal use, but especially nasal.

Suitable for this purpose are peptides and proteins which are composed of 3 to 225 amino acids, such as, for example, TRH (protirelin, thyroliberin), LHRH (gonadoliberin), chemically modified analog peptides of the hypothalamic regulatory hormones such as, for example, buserelin, somatostatin and cyclic somatostatin analogs, somatorelin (GRH) analogs, analog peptides of pituitary hormones such as, for example, the corticotropin analog alsactide (ACTH-17), calcium-regulating hormones (calcitonin, parathyroid hormone) and their analogs, as well as gastrointestinal hormones (for example secretin and cholecystokinin) and pancreatic hormones (insulin and insulin analogs). Those with 3 to 51 amino acids are particularly suitable.

The following may be particularly mentioned:

| Name of the peptide or protein | Used, for example, in: | Number of amino acids |
|---|---|---|
| Oxytocin | uterine inertia | 9 |
| Vasopressin | diabetes insipidus | 9 |
| Ornipressin | hemorrhages | 9 |
| Desmopressin | diabetes insipidus | 9 |
| Corticotropin (ACTH) | inflammatory disorders | 39 |

| Name of the peptide or protein | Used, for example, in: | Number of amino acids |
|---|---|---|
| Tetracosactide | inflammatory disorders | 24 |
| Alsactide | " | 17 |
| Insulin | diabetes mellitus | 51 |
| δ-Sleep-ind. peptide | sleep disturbances | 9 |
| Secretin | gastric hemorrhages | 27 |
| Cholecystokinin | biliary tract disorders, as appetite suppressant | 8-32 |
| Somatoliberin (GRH) | dwarfism | 44 |
| [D-Ala²] somato-liberin-(1-29) amide | " | 29 |
| Somatoliberinyl-glycine | " | 45 |
| Glucagon | hypoglycemia | 29 |
| Somatostatin | gastric hemorrhages | 14 |
| Octreotide | tumors | 8 |
| Spantide | substance P inhibition | 11 |
| Corticoliberin (CRF) | pituitary diagnostic aid | 41 |
| Bradykinin antagonists | pain, colds | 9-11 |
| Atriopeptin III | cardiac and renal insufficiency | 24 |
| ANF-(99-126) | cardiac and renal insufficiency | 28 |
| Thymopentin | rheumatoid arthritis | 5 |
| Interferon-α | colds | 125 |
| Thyroliberin (TRH) | pituitary diagnostic aid | 3 |
| Gonadoliberin (LHRH) | cryptorchidism, sterility | 10 |
| Buserelin | prostate cancer, endometriosis | 9 |
| Goserelin | prostate cancer, endometriosis | 10 |
| Triptorelin | prostate cancer, endometriosis | 10 |
| LH-RH-T | prostate cancer, endometriosis | 9 |
| Leuprorelin | prostate cancer, endometriosis | 9 |
| Lutrelin | prostate cancer, endometriosis | 9 |
| Nafarelin | prostate cancer, endometriosis | 10 |
| Histrelin | prostate cancer, endometriosis | 9 |
| Calcitonin | Paget's disease, osteoporosis | 32 |
| Elcatonin | " | 32 |
| Parathyroid hormone (1-34) | hypocalcemia | 34 |
| Sincalide | diagnostic aid for pancreatic function | 8 |
| Ceruletide | diagnostic aid for pancreatic function | 10 |
| Pentagastrin | diagnostic aid for gastric function | 5 |
| Desglugastrin | " | 7 |
| Ociltide | bowel-contracting | 5 |
| Angiogenin | vascular regeneration | 123 |
| TGF-beta | tumor therapy, immunosuppression | 224 |
| Hirudins | anticoagulation | 64-65 |

These peptides and proteins can be obtained by generally known processes, for example by Merrifield synthesis or genetic engineering and by isolation of naturally occurring peptides and proteins.

The invention also relates to pharmaceutical compositions containing a pharmacologically effective amount a) of one, two or three peptides or proteins, each composed of 3 to 225 amino acids, in particular of 3 to 51 amino acids, or the physiologically tolerated salts thereof, and b) of an aid of the general formula I

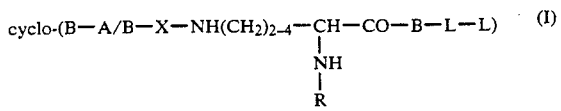

in which
B denotes a basic amino acid,
A/B denotes an acidic or basic amino acid,
X denotes a neutral and hydrophilic amino acid,
L denotes a lipophilic neutral amino acid, and
R denotes hydrogen or an acyl radical,
or the physiologically tolerated salts thereof in each case.

Preferred compositions are those which contain an aid of the formula I in which
B denotes lysine, ornithine, histidine, 2,4-diaminobutyric acid or arginine,
A/B denotes lysine, ornithine, histidine, 2,4-diaminobutyric acid, arginine, aspartic acid or glutamic acid,
X denotes asparagine, glutamine, serine or threonine,
L denotes leucine, isoleucine, valine, threonine, phenylalanine or tryptophan, and
R denotes hydrogen or an acyl radical having the following structures H—Dab—, H—Ser—, H—Ile—, H—Thr—Dab—,
H—Thr—Ser—, H—Dab—Thr—Dab—, H—Dab—Thr—Ser—,
H—Leu—Glu—Ile—, Ac—Dab—Thr—Dab—,
Ac—Dab—Thr—Ser—, Ac—Leu—Glu—Ile—, it being possible for each of the amino acids to be in the D or L form.

In this context, Ac represents

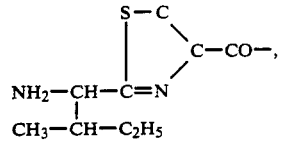

it being possible for S also to be in the form of the sulfoxide or sulfone, and for the double bond to be hydrogenated,

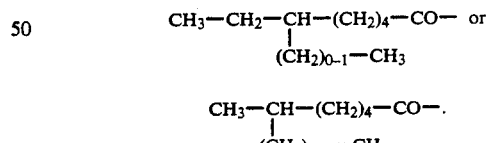

Of particular interest are those compositions which contain an aid selected from the group comprising bacitracin A, colistin A or B, circulin A or B, polymyxin B₁ or B₂, or polymyxin D₁ or D₂.

The pharmaceutical compositions according to the invention furthermore preferably contain a peptide or protein composed of 3 to 225 amino acids, in particular a peptide or protein having 3 to 51 amino acids.

However, compositions composed of two or three different peptides and/or proteins such as, for example, corticotropin +LHRH+GRH or protirelin+LHRH+GRH in conjunction with an aid such as, for example, bacitracin are also of interest, especially for use as diagnostic agents.

The dose of the peptides and/or proteins and of the aids when used in mammals, preferably in humans, in the compositions or products according to the invention is in the range 10 μg to 10 mg for each peptide/protein and use, and that for the aid is a concentration of $10^{-5}$ to $10^{-1}$ mol/l for each use, preferably between $10^{-4}$ and $10^{-2}$ mol/l.

The compositions according to the invention can be used by being administered onto the mucosa, i.e. nasally, buccally, rectally or vaginally. Nasal administration is preferred in this connection.

The pharmacologically utilizable combinations of the present invention, and the salts thereof, can be used to prepare pharmaceutical products which contain an effective amount of the active substances, together with vehicles, and which are suitable for administration onto the mucosa, such as, for example, tablets, suppositories, capsules, gels, films, emulsions, suspensions, aerosols, solutions or sprays (Sucker, Fuchs, Speiser, Pharmazeutische Technologie (Pharmaceutical Technology) published by Georg Thieme 1978).

The following are preferably used:

1. Aqueous or Aqueous-Alcoholic Solutions for Administration with a Dropper or with a Plastic Squeeze Bottle or for Nebulization with a Metering Atomizer Pump The composition can contain, besides the active substance and the absorption promoter, a tonicity additive, for example sodium chloride, potassium nitrate, potassium sodium phosphate, polyalcohols such as, for example, glucose, mannitol or sorbitol, buffer substances such as, for example, potassium sodium phosphate, citric acid and the salts thereof, as well as mixtures of the two in order to adjust to a pH range of 3 to 8, a preservative, for example benzalkonium chloride, benzyl alcohol, 1,1,1-trichloro-2-methyl-2-propanol or methyl 4-hydroxybenzoate, a chelating agent, for example sodium EDTA and, as solvent, water or mixtures or water with $(C_1-C_4)$-alkanols. The solution is administered with a suitable apparatus or is sprayed into the nose or onto the oral mucosa.

2. Aqueous or Aqueous-Alcoholic Gels for Introduction into Body Cavities (Mouth, Nose, Rectum or Vagina)

In addition to 1., a gel contains an additive increasing the viscosity, for example a polyacrylate polymer or a cellulose ether such as, for example, hydroxypropylmethylcellulose (HPMC), hydroxyethylcellulose (HEC) or methylhydroxyethylcellulose (MHEC).

3. Suspensions in Propellant Gases

The composition can contain besides the micronized active substance and the micronized absorption promoter a fluorinated hydrocarbon, for example ®Frigen F 113, and a suspending aid, for example sorbitan trioleate.

Suitable propellant gases are fluorinated hydrocarbons, for example ®Frigen F 12 and ®Frigen F 114, as well as mixtures thereof. The containers can be filled in a manner known per se by the cold-filling process or else by pressure filling.

4. Triturations with Vehicles in Capsules for Intranasal Use or Inhalation

The micronized substances (active substance and absorption promoter) are used, where appropriate after addition of an agent to improve the flow properties, such as, for example, lactose, to fill hard gelatin capsules. Intranasal or pulmonary administration of the contents of a capsule is effected with an aid to inhalation which allows the powder to be converted into an inhalable aerosol.

5. Buccal Forms

The active substance and absorption promoter can be in dissolved or suspended form. Suitable drug forms are compressed or laminated products composed of mixtures of active substance and absorption promoter in polymers. Suitable polymers are cellulose ethers (for example HPMC, carboxymethylcellulose (CMC) or polyacrylates.

The examples which follow are intended to explain the present invention without restricting the invention to the compositions mentioned as representatives:

EXAMPLE 1

| Nasal solution | |
|---|---|
| Buserelin | 0.15 mg |
| Bacitracin | 1.50 mg |
| Sodium chloride | 0.80 mg |
| Citric acid.H$_2$O | 0.11 mg |
| Sodium citrate.2H$_2$O | 0.15 mg |
| Benzalkonium chloride | 0.01 mg |
| Disodium EDTA | 0.01 mg |
| Water (purified) | to 0.1000 ml |

EXAMPLE 2

| Gel | |
|---|---|
| [D-Ala$^2$] Somatorelin-(1-29) amide | 0.020 mg |
| Colistin | 1.200 mg |
| Polyacrylic acid 940 | 0.400 mg |
| Sodium hydroxide solution 15% | 0.900 mg |
| Glycerol | 15.000 mg |
| Methyl 4-hydroxybenzoate | 0.150 mg |
| Purified water | to 100.000 mg |

EXAMPLE 3

| Suppository | |
|---|---|
| Salmon calcitonin | 0.200 mg |
| Polymyxin | 1.000 mg |
| Suppository base (hard fat) | to 2.500 g |

EXAMPLE 4

| Diagnostic agent | |
|---|---|
| Protirelin | 0.050 mg |
| Gonadoliberin | 0.025 mg |
| Somatoliberin | 0.025 mg |
| Bacitracin | 0.250 mg |
| Citric acid.H$_2$O | 0.170 mg |
| Disodium monohydrogen phosphate.12H$_2$O | 1.100 mg |
| Sodium chloride | 0.600 mg |
| Benzyl alcohol | 1.000 mg |

| Diagnostic agent | |
|---|---|
| Purified water | to 0.100 ml |

We claim:

1. A method for promoting the absorption of peptides and proteins on administration onto the mucosa which comprises administering in an effective amount a cyclic peptide or a physiologically tolerated salt thereof.

2. The method as claimed in claim 1, wherein a cyclic peptide of the formula I

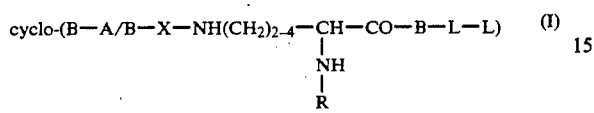

in which
B denotes a basic amino acid,
A/B denotes an acidic or basic amino acid,
X denotes a neutral and hydrophilic amino acid,
L denotes a lipophilic neutral amino acid, and
R denotes hydrogen or an acyl radical,
is used.

3. The method as claimed in claim 1, wherein a cyclic peptide of the formula I in which
B denotes lysine, ornithine, histidine, 2,4-diaminobutyric acid or arginine,
A/B denotes lysine, ornithine, histidine, 2,4-diaminobutyric acid, arginine, aspartic acid or glutamic acid,
X denotes asparagine, glutamine, serine or threonine,
L denotes leucine, isoleucine, valine, threonine, phenylalanine or tryptophan, and
R denotes hydrogen or an acyl radical having the following structures H—Dab—, H—Ser—, H—Ile—, H—Thr—Dab—,
H—Thr—Ser—, H—Dab—Thr—Dab—, H—Dab—Thr—Ser—,
H—Leu—Glu—Ile—, Ac—Dab—Thr—Dab—,
Ac—Dab—Thr—Ser—, Ac—Leu—Glu—Ile—, it being possible for each of the amino acids to be in the D or L form, and Ac represents here

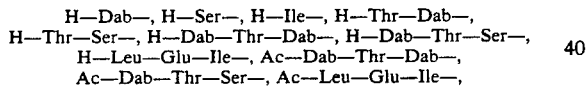

it being possible for S also to be in the form of the sulfoxide or sulfone, and for the double bond to be hydrogenated,

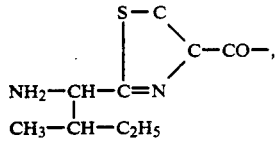

is used.

4. The method as claimed in claim 1 wherein the cyclic peptide is selected from the group consisting of bacitracin A, colistin A or B, circulin A or B, polymyxin $B_1$ or $B_2$, and polymyxin $D_1$ or $D_2$.

5. A pharmaceutical composition containing a pharmacologically effective amount
   a) of one, two or three peptides or proteins, each composed of 3 to 225 amino acids, or the physiologically tolerated salts thereof, and
   b) of a cyclic peptide of the formula I

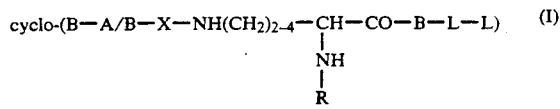

in which
B denotes a basic amino acid,
A/B denotes an acidic or basic amino acid,
X denotes a neutral and hydrophilic amino acid,
L denotes a lipophilic neutral amino acid, and
R denotes a hydrogen or an acyl radical,
or the physiologically tolerated salts thereof in each case.

6. A composition as claimed in claim 5, wherein
B denotes lysine, ornithine, histidine, 2,4-diaminobutyric acid or arginine,
A/B denotes lysine, ornithine, histidine, 2,4-diaminobutyric acid, arginine, aspartic acid or glutamic acid,
X denotes asparagine, glutamine, serine or threonine,
L denotes leucine, isoleucine, valine, threonine, phenylalanine or tryptophan, and
R denotes hydrogen or an acyl radical having the following structures H—Dab—, H—Ser—, H—Ile—, H—Thr—Dab—,
H—Thr—Ser—, H—Dab—Thr—Dab—, H—Dab—Thr—Ser—,
H—Leu—Glu—Ile—, Ac—Dab—Thr—Dab—,
Ac—Dab—Thr—Ser—, Ac—Leu—Glu—Ile—, it being possible for each of the amino acids to be in the D or L form, and Ac represents here

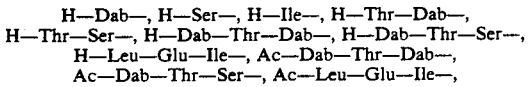

it being possible for S also to be in the form of the sulfoxide or sulfone, and for the double bond to be hydrogenated,

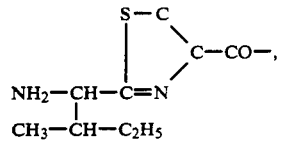

7. A composition as claimed in claim 5, wherein a cyclic peptide selected from the group comprising bacitracin A, colistin A or B, circulin A or B, polymyxin $B_1$ or $B_2$, or polymyxin $D_1$ or $D_2$ is used.

8. A composition as claimed in claim 5, wherein a peptide or protein having 3 to 225 amino acids is used.

9. A composition as claimed in claim 5, wherein a peptide or protein composed of 3 to 51 amino acids is used.

* * * * *